(12) United States Patent
DeSalvo et al.

(10) Patent No.: US 7,755,755 B2
(45) Date of Patent: Jul. 13, 2010

(54) MATCHED OPTICAL WAVEFORMS FOR DETECTION AND IDENTIFICATION OF BIOLOGICAL PATHOGENS

(75) Inventors: John Richard DeSalvo, Satellite Beach, FL (US); Geoffrey Lynn Burdge, Merritt Island, FL (US); Bruce W. FitzGerald, Vail, AZ (US); Young-Kai Chen, Berkley Heights, NJ (US); Andreas Leven, Gillette, NJ (US); Peter Delfyett, Geneva, FL (US)

(73) Assignees: Harris Corporation, Melbourne, FL (US); Lucents Technologies Inc., Murray Hills, NJ (US); University of Central Florida Foundations, Inc., Orlando, FL (US)

( * ) Notice: Subject to any disclaimer, the term of this patent is extended or adjusted under 35 U.S.C. 154(b) by 699 days.

(21) Appl. No.: 11/705,926

(22) Filed: Feb. 14, 2007

(65) Prior Publication Data

US 2008/0195335 A1 Aug. 14, 2008

(51) Int. Cl.
*G01J 3/28* (2006.01)
(52) U.S. Cl. ................................... 356/300
(58) Field of Classification Search ............ None
See application file for complete search history.

(56) References Cited

U.S. PATENT DOCUMENTS

| 3,829,694 A | * | 8/1974 | Goto | ............ 250/339.11 |
| 5,450,193 A | * | 9/1995 | Carlsen et al. | ............ 356/301 |
| 5,939,721 A | | 8/1999 | Jacobsen | |
| 6,723,991 B1 | | 4/2004 | Sucha | |
| 2007/0019282 A1 | | 1/2007 | Weiner | |

FOREIGN PATENT DOCUMENTS

EP 1318389 6/2003

OTHER PUBLICATIONS

Scully et al.: "Fast Cars: Engineering a Laser Spectroscopic Technique for Rapid Identification of Bacterial Spores"; Proceedings of the National Academy of Sciences; vol. 99, No. 17, (Aug. 20, 2002).
Delfyett et al.: "Optical Frequency Combs From Semiconductor Lasers and Applications in Ultrawideband Signal Processing and Communications"; Journal of Lightwave Technology IEEE; vol. 24, No. 7 (Jul. 2006).
Ding et al.: "Widely Tunable Monochromatic THz Sources Based on Phase-Matched Difference-Frequency Generation in Nonlinear-Optical Crystals: A Novel Approach"; Laser Physics Maik Nauka-Interperiodica Publishing Ru; vol. 16, No. 4 (Apr. 2006).
Mejean, et al.: "Remote Detection and Identification of Biological Aerosols Using a Femtosecond Terawatt Lidar System"; Applied Physics B: Lasers and Ooptics, vol. 78, No. 5 (Mar. 2004).

* cited by examiner

*Primary Examiner*—Tu T Nguyen
(74) *Attorney, Agent, or Firm*—Harness, Dickey & Pierce, P.L.C.

(57) ABSTRACT

A method is provided for identifying a contaminant in a gaseous space. The method includes: generating a broadband optical waveform; shaping the optical waveform to match an expected waveform for a known contaminant; and transmitting the shaped optical waveform towards an unknown contaminant. Upon receiving a reflected optical waveform from the unknown contaminant, determining whether the unknown contaminant correlates to the known contaminant based on the reflected waveform.

16 Claims, 4 Drawing Sheets

MATCHED OPTICAL WAVEFORMS FOR DETECTION AND IDENTIFICATION OF BIOLOGICAL PATHOGENS

FIELD

The present disclosure relates generally to a method for identifying a contaminant in a gaseous space and, more particularly, to a robust system and method for detecting and identifying biological pathogens and chemical contaminants, or identifying the presence of a specific chemical specie produced by a tag.

BACKGROUND

Chemical and biological agents pose a real and unpredictable threat to mankind. A wide variety of synthetic chemicals, toxins and biological materials have been developed for use as warfare or terror agents. Some chemical and biological agents are readily available and could easily be prepared in large quantities. Detecting chemical and biological agents quickly and accurately at very low concentration levels is crucial to a successful defense against the use of such agents as weapons.

Chemical effluent from chemical processing plants or factories, from leakage of fuels such as rocket propellants, or from volatility of chemical tags specifically placed in medicines or explosives also needs to be detected with sensitivity either remotely or in close proximity.

Since chemical and biological agents are effective in small doses, sensitivity is a critical feature of any detection system. Complex and rapidly changing operating conditions also require a detection system to exhibit a high degree of selectivity. In other words, selectivity is needed to discriminate chemical and biological agents from other harmless materials present in the environment. Lastly, the speed in which an agent is identified is essential for determining an appropriate response to a threatening condition. Moreover, speed is an important characteristic in that the response of multiple agents can be searched for during the scan. Therefore, it is desirable to provide a detection scheme which addresses each of these technical challenges.

The statements in this section merely provide background information related to the present disclosure and may not constitute prior art.

SUMMARY

A method is provided for identifying a contaminant in a gaseous space. The method includes: generating a broadband optical waveform; shaping the optical waveform to match an expected spectral waveform for a known contaminant; and transmitting the shaped optical waveform towards an unknown contaminant. Upon receiving the reflected waveform from the unknown contaminant, a detection system determines whether or not the unknown contaminant correlates to a known contaminant based on the spectrally reflected waveform. The absorption spectra of the contaminants are typically unique and measurable.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
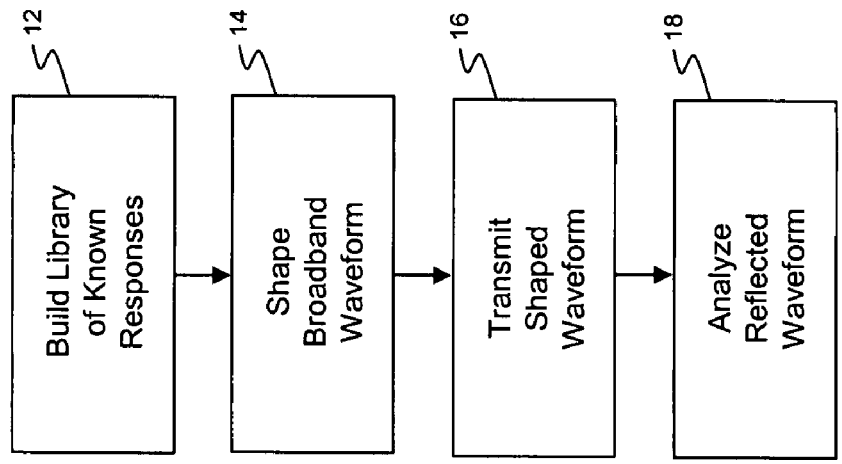
FIG. 1 is a flowchart illustrating a method for identifying biological pathogens.

FIG. 1 illustrates a method for identifying biological pathogens, chemical contaminants or the presence of a chemical tag based on the principles of spectroscopic detection. Prior to identifying an unknown pathogen, a library of spectroscopic responses is compiled for pathogens of interest as indicated at 12. In an exemplary embodiment, a spectroscopic response (i.e., an expected waveform) for a given biological pathogen may be determined by transmitting a broadband optical waveform towards a known biological pathogen of interest. The waveform as reflected by the biological pathogen of interest is then captured and stored in a library as the spectroscopic response for the biological pathogen. To improve the sensitivity and selectivity of the detection process, the optical waveform reflected by the biological pathogen of interest may be partitioned into a plurality of spectral components (e.g., waveforms having different frequency ranges). The spectroscopic response at each of the different spectral components is captured and stored in the library, thereby creating a series of expected waveforms for a given biological pathogen. This process is in turn repeated for a variety of different biological pathogens of interest to create an entire library.

To identify an unknown biological pathogen, a broadband optical waveform is first shaped at 14 to match an expected waveform for a known biological pathogen. Shaping is understood to mean adjusting the amplitude and/or phase of some or all of the spectral components of the waveform. By shaping the interrogating waveform to match the expected waveform, only light that is expected to exhibit a spectroscopic response is transmitted towards the target. In other words, light which will not be used in the detection process is not transmitted towards the target, thereby maximizing the signal-to-noise ratio of the reflected waveform. The shaped waveform is transmitted at 16 towards an unknown biological pathogen and the spectroscopic response embodied in the reflected waveform is analyzed at 18 to determine whether the unknown biological pathogen correlates to the known biological pathogen. The unknown biological pathogen is identified when the spectroscopic response of a reflected waveform matches the spectroscopic response of the known biological pathogen.

Different waveforms or pulses of a waveform may be used to interrogate the unknown biological pathogen. Each different waveform or pulse of a waveform is shaped to match an expected waveform for a known biological pathogen found in the library and then transmitted towards the unknown biological pathogen. In this way, the unknown biological pathogen may be evaluated in relation to each known pathogen. While the following description is provided with reference to biological pathogens, it is readily understood that this technique is suitable for detecting and/or identifying chemical agents, toxins, and other types of contaminants which may be found in a gaseous volume.

Figure 2:
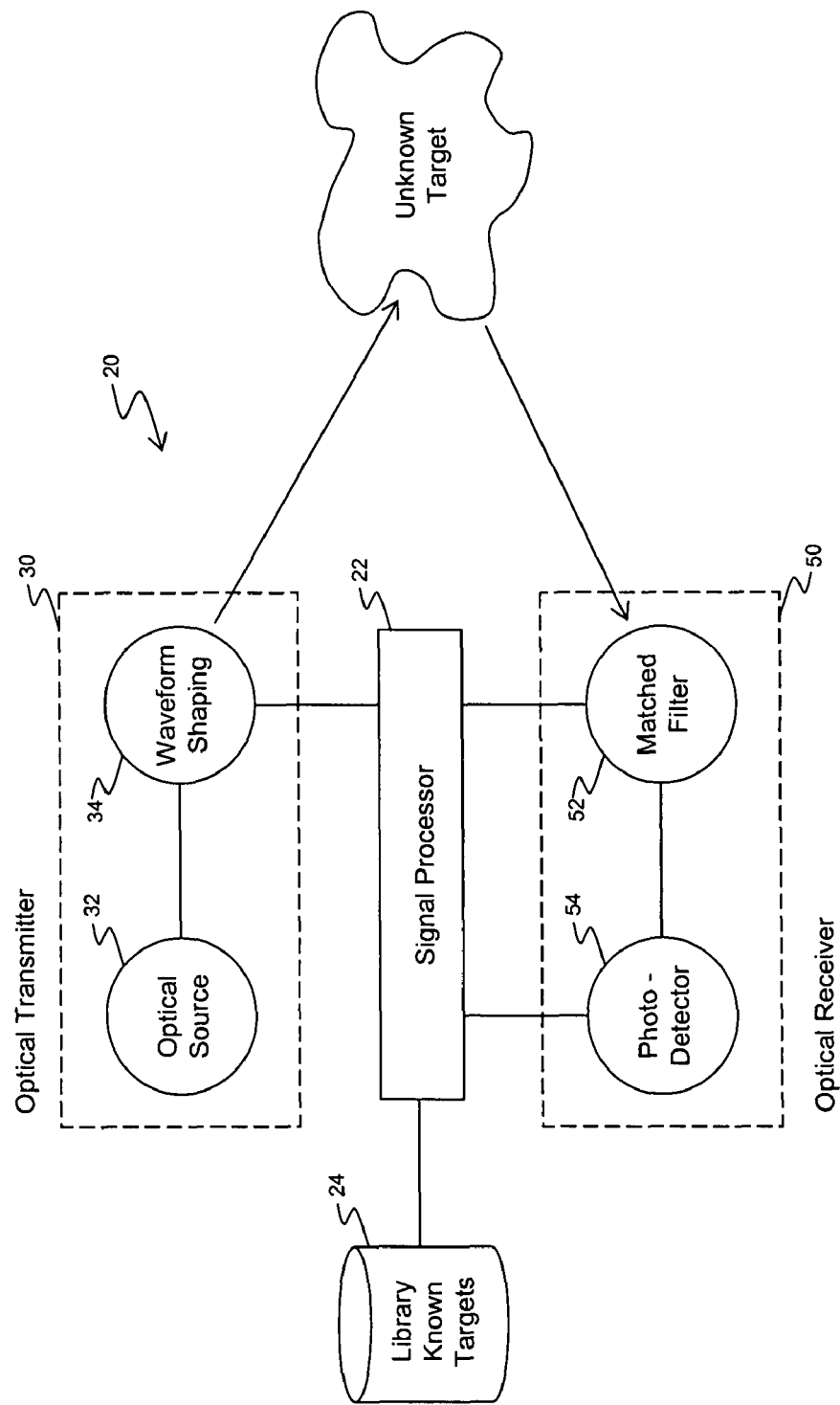
FIG. 2 is a block diagram of an exemplary system for detecting and identifying biological pathogens or chemical contaminants.

FIG. 2 depicts an exemplary system 20 for detecting and identifying biological pathogens. The detection system 20 is generally comprised of an optical transmitter 30, an optical receiver 50, a digital signal processor 22, and a library 24 of spectroscopic responses for known biological pathogens. The optical transmitter 30 includes an optical source 32 and a waveform shaping component 34. The optical receiver 50 includes a filtering component 52 and a photodetector 54. Each of these components is further described below.

The optical source 32 generates a pulsed broadband optical waveform operating in the Terahertz frequency range with a Giga-pulse repetition rate. Each pulse or series of pulses may be used to interrogate an unknown contaminant. Operating at such high repetition rates increases the speed at which detection can occur; whereas, the use of a broadband Terahertz waveform improves the selectivity of the system as further described below.

Figure 3:
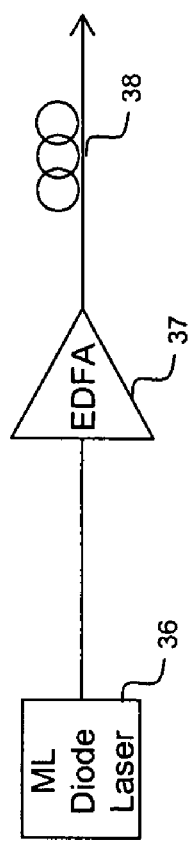
FIG. 3 is a diagram of an exemplary optical source which may be used in the detection system.

In an exemplary embodiment, the optical waveform is further defined as a supercontinuum waveform (i.e., a waveform with a very broad spectral bandwidth generated by a nonlinear process). A supercontinuum waveform may be generated using various techniques. For example, a supercontinuum waveform may be generated by spectrally broadening (i.e., increasing the number of spectral components) an optical waveform by propagating it through some nonlinear medium, such as a crystal. FIG. 3 illustrates an exemplary technique, where the optical source 32 is implemented using a 10 Gigahertz comb stabilized, mode-locked laser 36 operably connected to a nonlinear fiber 38. An optical amplifier 37 (e.g., an erbium-doped fiber amplifier) may be interposed between the laser 36 and the non-linear fiber 38. It is envisioned that other types of pulsed light sources (e.g., a fiber ring laser) may be used. Likewise, other techniques for broadening the optical spectrum of the optical waveform across a range of frequencies are also contemplated by this disclosure. For instance, the pulsed light source may be passed through other mediums that cause self-phase modulation to broaden the spectrum of the individual pulses. Alternatively, a supercontinuum waveform may be achieved using techniques such as Raman scattering or four-wave mixing.

Figure 4:
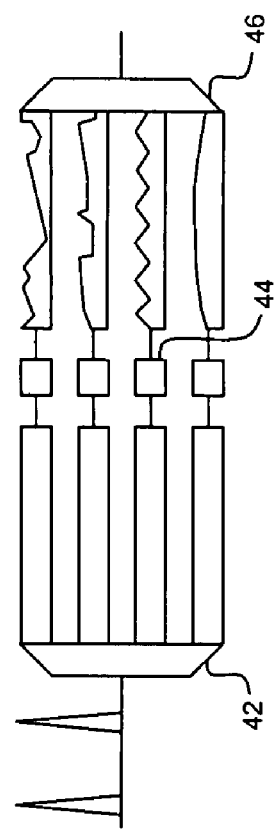
FIG. 4 is a diagram of an exemplary waveform shaping component which may be used in the detection system.

FIG. 4 depicts an exemplary embodiment of a waveform shaping component. In this exemplary embodiment, the broadband optical waveform is preferably shaped across a range of different frequencies embodied in the waveform. Thus, light from optical source 32 is input into a demultiplexer 42. The demultiplexer 42 partitions the broadband optical waveform into a plurality of optical waveforms traversing different adjacent frequency ranges. Optical waveforms at four different frequency ranges are shown as being output from the demultiplexer 42. It is readily understood that more or less waveforms be output by the demultiplexer 42 or a series of multiplexers. A plurality of optical modulators 44 are in turn coupled to the demultiplexer 42, such that each optical modulator receives one of the optical waveforms output from the demultiplexer 42. Each of the optical modulators is further controlled by the signal processor 22 which is in data communication with a data store of expected waveforms. However, it is contemplated that the waveform may be shaped using a single optical modulator.

In operation, the optical waveforms at each of the different frequencies may be shaped by one of the optical modulators in accordance with the expected spectroscopic response (i.e., waveform) for the biological pathogen of interest. In other words, the optical waveform at a first frequency is modulated in accordance with the expected spectroscopic response at the first frequency and the optical waveform at a second frequency is modulated in accordance with the expected spectroscopic response at the second frequency. The resulting waveforms are then input into a multiplexer 46 that recombines the waveforms into a single broadband optical waveform. In a less sophisticated approach, wavelength blockers may be used in place of the optical modulators. Wavelengths which are expected to exhibit a spectroscopic response are passed; whereas, wavelength which are not expected to exhibit a spectroscopic response are completely blocked and thus eliminated from the interrogating waveform. It is readily understood that other types of shaping or filtering mechanisms may be used in place of optical modulators.

To interrogate an unknown target, each pulse of light (or series of pulses) may be shaped to matched to an expected waveform for a known biological pathogen in the manner described above. In this way, the unknown target may be compared to hundreds of thousands of known biological pathogens in a very short amount of time. When the unknown target extends outside the field of view of the optical transmitter, the transmitter may be scanned to interrogate a larger target area. In this case, the interrogating waveform at each scan location will match a single biological pathogen until the entire target area has been scanned. The interrogating waveform can then be matched to a different biological pathogen and the target area can be re-scanned. Alternatively, different pulses of light may be matched to different biological pathogen at a given scan location. Once an interrogating waveform has been transmitted for the series of biological pathogens of interest, the optical transmitter may be moved to a different scan location and the process repeated until the entire target area has been scanned.

On the receiver side, an optical matched filter is preferably employed to further improve the selectivity of the detection system. Knowing the biological pathogen of interest, the optical matched filter may be controlled by the signal processor to filter the reflected waveform in accordance with the expected waveform for the biological pathogen. Further details regarding an exemplary optical matched filter may be found in U.S. Provisional Patent No. 60/803,460 filed on May 30, 2006 and entitled "RF MATCHED FILTER RECEIVER USING OPTICAL TECHNIQUES, ASSOCIATED BEAMFORMING AND ASSOCIATED METHODS" which is incorporated herein by reference. Although not limited hereto, auto-correlating the incoming reflected waveform to the interrogating waveform is one exemplary filtering technique. Other filtering techniques that rely upon the expected spectroscopic response are also contemplated by this disclosure.

Different detection schemes may be employed to assess the reflected waveforms. In FIG. 5A, the reflected waveform is split into a plurality of identical intensity split waveforms by an optical splitter 62. A plurality of optical matched filters 64 are coupled to the optical splitter 62 such that each optical matched filter receives one of the waveforms output from the splitter 62. Each of the optical matched filters 64 is further controlled by the signal processor 22. In this way, each waveform may be filtered at a different frequency. For instance, a first waveform is filtered to only pass the expected spectroscopic response at a first frequency; whereas, a second waveform is filtered to only pass the expected spectroscopic response at a second frequency. The filtered waveforms are then input into a signal combiner 66 that recombines the waveforms into a single waveform. Lastly, a photodetector 68 operable over the entire spectral bandwidth of the interrogating waveform converts the waveform into an analog signal.

When the reflected waveform from the target correlates to the expected waveform, the matched filters have passed the expected spectroscopic response onto the photodetector while filtering out most of the noise. Conversely, when the target does not correlate to the expected waveform, the matched filters have filtered out most of the reflected waveform. Thus, an amplitude threshold detection scheme can be used to determine whether the target correlates to the expected biological pathogen. In an exemplary embodiment, the signal output from the photodetector 68 is input into an analog-to-digital converter which is in turn coupled to the signal processor. The threshold detection scheme may be implemented in software and executed by the signal processor in a manner known in the art.

Figure 5A:
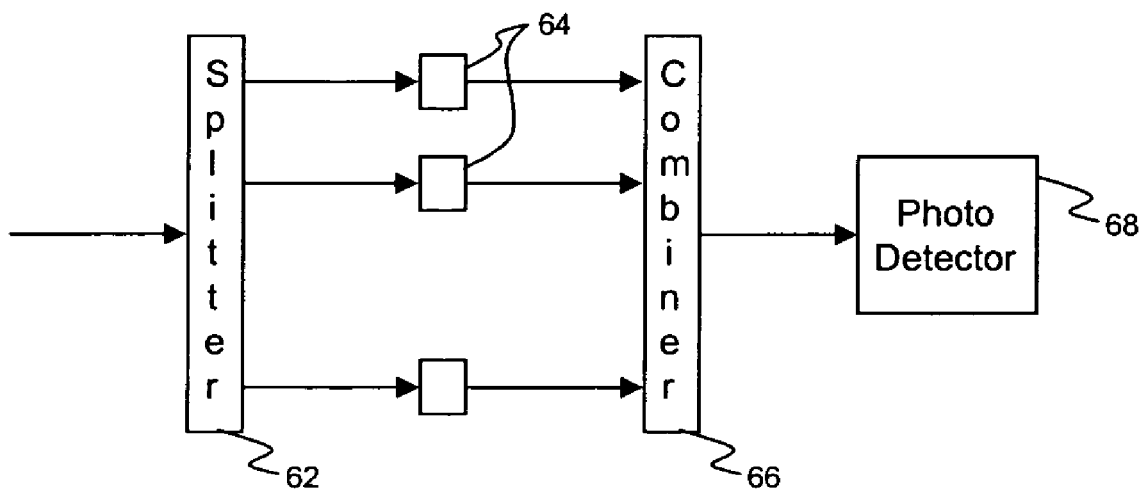
FIGS. 5A and 5B are block diagrams depicting exemplary detection schemes which may be used in the detection system.
Figure 5B:
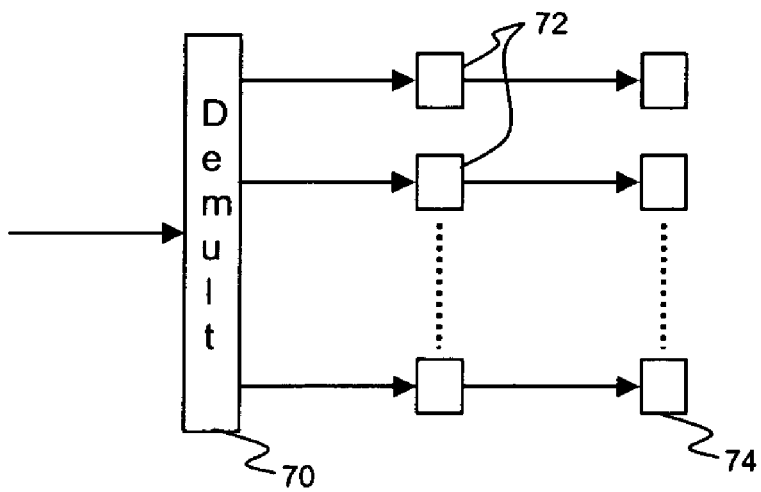

In an alternative approach, detection is based on an assessment of each frequency component of the reflected waveform as shown in FIG. 5B. In this approach, the reflected waveform is input into a demultiplexer 70 which partitions the waveform into a plurality of waveforms having different frequencies. Each waveform is again filtered by one of a plurality of optical filters 72 in accordance with the expected waveform at a given frequency. However, each filtered waveform is input into a different photodetector 74, such that post-processing signal analysis can be performed on each frequency component to determine whether the target correlates to the expected biological pathogen. It is readily understood that other detection schemes fall within the broader aspects of this disclosure.

The above description is merely exemplary in nature and is not intended to limit the present disclosure, application, or uses.

What is claimed is:

1. A method for identifying a contaminant in a gaseous space, comprising:
    determining a spectroscopic response for a plurality of known contaminants;
    generating a broadband optical waveform;
    shaping the optical waveform concurrently at a plurality of different frequencies to match the spectroscopic response for the plurality of known contaminants;
    transmitting the shaped optical waveform towards an unknown contaminant;
    receiving a reflected portion of the shaped optical waveform that is reflected by the unknown contaminant;
    splitting the reflected portion of the shaped optical waveform into a plurality of received optical waveforms;
    filtering each of the plurality of received optical waveforms at a different one of the plurality of frequencies;
    recombining the plurality of received optical waveforms to form one received waveform; and
    determining whether the unknown contaminant correlates to one of the plurality of known contaminants based on the one received waveform.

2. The method of claim 1 wherein generating a broadband optical waveform further comprises generating a supercontinuum optical waveform.

3. The method of claim 1 wherein shaping the optical waveform further comprises adjusting at least one of an amplitude or a phase of the optical waveform.

4. The method of claim 3 wherein determining the spectroscopic response for the plurality of known contaminants further comprises:

transmitting an initial broadband optical waveform towards each of the plurality of known contaminants;
receiving the initial broadband optical waveform as spectrally reflected by each of the plurality of known contaminants;
partitioning the spectrally reflected initial broadband optical waveform into a plurality of optical waveforms having different frequency ranges; and
determining an expected waveform at each of the different frequency ranges.

5. The method of claim 1 further comprises determining a spectroscopic response for the plurality of known contaminants prior to generating a broadband optical waveform.

6. The method of claim 1 wherein shaping the optical waveform further comprises blocking the optical waveform at frequencies where the expect waveform does not exhibit a spectroscopic response.

7. The method of claim 1 wherein shaping the optical waveform further comprises optically modulating the optical waveform at each of the frequencies where the expected reflected waveform exhibits a spectroscopic response.

8. The method of claim 1 wherein receiving the shaped optical waveform further comprises filtering the shaped optical waveform based on the expected reflected waveform for the plurality of known contaminants.

9. The method of claim 1 wherein receiving the shaped optical waveform further comprises auto-correlating the shaped optical waveform to the expected reflected waveform for the plurality of known contaminants.

10. A system for identifying a contaminant in the atmosphere, comprising:
    an optical source operable to generate a supercontinuum waveform;
    a data store operable to store a plurality of expected waveforms, where each expected waveform correlates to a waveform expected to receive from a known contaminant; and
    a waveform shaping component adapted to receive the supercontinuum waveform from the optical source, the waveform shaping component operable to select one of the plurality of expected waveforms from the data store and optically modulate the supercontinuum waveform in accordance with the selected expected waveform, wherein the waveform shaping component further comprises a demultiplexer configured to receive the supercontinuum waveform and operable to partition the supercontinuum waveform into a plurality of waveforms each in a different frequency range; a plurality of optical modulators connected to the demultiplexer, such that each optical modulator receives one of the plurality of waveforms and is operable to optically modulate the waveform in accordance with the selected expected waveform from the data store; and a multiplexer connected to the plurality of optical modulators and operable to combine the plurality of modulated waveforms to form an optical output waveform.

11. The system of claim 10 wherein the optical source further comprises a pulsed light source operating in at Terahertz frequency which is operable to output a pulsed stream of light into an optical medium so as to cause self-phase modulation of the pulsed stream of light.

12. The system of claim 10 wherein the optical source is further defined as a mode-locked laser operably connected to a nonlinear optical fiber.

13. The system of claim 12 further comprises an optical amplifier interposed between the diode laser and the nonlinear optical fiber.

14. The system of claim 10 further comprises an optical match filter configured to receive the waveform as reflected by an unknown contaminant and operable to filter the reflected waveform in accordance with an expected waveform selected from the data store.

15. The system of claim 10 further comprises
an optical splitter configured to receive the waveform reflected by an unknown contaminant and operable to intensity split the reflected waveform into a plurality of reflected waveforms; and
a plurality of optical filters optically coupled to the optical splitter and operable to filter each of the plurality of reflected waveforms at a different frequency.

16. A detection system for identifying a contaminant in the atmosphere, comprising:
a data store operable to store a plurality of expected waveforms, where each expected waveform correlates to a spectroscopic response for a known contaminant;
an optical source operable to generate a supercontinuum waveform for transmission towards an unknown contaminant;
a waveform shaping component configured to receive the supercontinuum waveform from the optical source and operable to optically modulate the waveform at one or more different frequencies embodied therein;
an optical match filter configured to receive a reflected portion of the waveform that is reflected by the unknown contaminant and operable to auto-correlate the reflected portion of the waveform to an expected waveform selected from the data store; and
a photodetector operable to capture the filtered waveform from the optical matched filter.

* * * * *